United States Patent [19]
Hampson et al.

[11] Patent Number: 6,066,457
[45] Date of Patent: May 23, 2000

[54] GLOBAL AMPLIFICATION OF NUCLEIC ACIDS

[75] Inventors: Ian Noel Hampson; Lynne Hampson, both of Cheshire, United Kingdom

[73] Assignee: Cancer Research Campaign Technology Limited, London, United Kingdom

[21] Appl. No.: 09/069,202

[22] Filed: Apr. 29, 1998

[30] Foreign Application Priority Data

Aug. 29, 1996 [GB] United Kingdom .................... 9618050

[51] Int. Cl.[7] ................................ C12Q 1/68; C12P 19/34
[52] U.S. Cl. ............................................... 435/6; 435/91.2
[58] Field of Search ................................ 435/6, 91.2, 91.1

[56] References Cited

U.S. PATENT DOCUMENTS 5,545,522  8/1996  Van Gelder et al. ........................ 435/6

FOREIGN PATENT DOCUMENTS 2 093 567  4/1993  Canada .
0 395 398  4/1990  European Pat. Off. .
94/11383   5/1994  WIPO .

OTHER PUBLICATIONS

Patanjali, S.R., et al., Construction of a Uniform–Abundance (Normalized CDNA Library, Proceedings of the National Academy of Sciences of USA, Mar. 1, 1991, vol. 88, No. 5, pp. 1943–1947, XP000368687.

Hampson I.N. et al., Chemical Cross Linking Subtraction (CCLS): A New Method for the Generation of Subtractive Hybridisation Probes, Nucleic Acids Research, 1992, vol. 20, No. 11, p. 2899 XP002050204.

Sharma, P. et al., PCR–Based Construction of Subtractive CDNA Library Using Magnetic Beads, Biotechniques, Oct. 1, 1993, vol. 15, No. 4, pp. 610,612 XP000402905.

Ermolaeva, O.D. et al., Subtractive Hybridization, A Technique for Extraction of DNA Sequences Distinguishing Two Closely Related Genomes: Critical Analysis, Genetic Analysis: Biomolecular Engineering, Jul. 1996, vol. 13, No. 2, pp. 49–58 XP000635153.

Hampson, I.N., et al., Directional Random Oligonucleotide Primed (DROP) Global Amplification of CDNA: Its Application to Subtractive CDNA Cloning, Nucleic Acids Research, 1996, vol. 24, No. 23, pp. 4832–4835.

*Primary Examiner*—Eggerton A. Campbell
*Attorney, Agent, or Firm*—Pillsbury Madison & Sutro LLP

[57] ABSTRACT

Nucleic acid starting material composed of a collection of single stranded nucleic acid molecules is anchored and processed by a direction random printing method to produce a mixture of shorter random size DNA molecules well-suited for achieving substantially uniform global PCR amplification. The processing and global amplification method disclosed is especially useful in conjunction with subtractive hybridization procedures applied, for example, to the study of differential gene expression.

28 Claims, 3 Drawing Sheets

Fig. 3

Biotinylated T7 Random Hexamer Primer
Biotin-5' TGTAATACGACTCACTATAGGGAG(N)₆ 3'  (SEQ ID NO: 1)

Biotinylated T7 Primer
Biotin-5' TCTAATACGACTCACTATAGGGAG 3'  (SEQ ID NO: 2)

T7 Primer
5' TGTAATACGACTCACTATAGGGAG 3'  (SEQ ID NO: 2)

R1 Random Hexamer Primer
5' ATGAGAATTCGACGTCAGCCAGC(N)₆ 3'  (SEQ ID NO: 3)

R1 Primer
5' ATGAGAATTCGACGTCAGCCAGC 3'  (SEQ ID NO: 4)

GLOBAL AMPLIFICATION OF NUCLEIC ACIDS

FIELD OF THE INVENTION

The present invention lies in the field of molecular biology and is particularly concerned with a technique for global amplification of nucleic acids, especially although not exclusively mRNA or cDNA derived therefrom corresponding to gene nucleotide sequences. The technique of this invention can be particularly useful when used in conjunction with subtractive hybridization applied, for example, to the study of differential gene expression between related tissue cells.

BACKGROUND OF THE INVENTION

Subtractive hybridization is a process that is commonly used in association with cloning of cDNA derived from mRNA extracted from particular cells that are under investigation and is most useful for producing DNA hybridization probes that can be utilised as screening agents to detect or locate DNA, in clone colonies or cDNA libraries for example, related to genes that are differentially expressed as compared with genes of other cells that exhibit different gene expression characteristics. This technique may, for example, be used in cancer research for comparing the gene products of tumour tissue cells with those of corresponding normal tissue cells in order to study the genetic changes that have occurred at the nucleic acid level. Probes obtained using this technique which are specific to DNA whose expression characteristics are modified by such genetic changes may be useful not only for carrying out genetic screening in connection with cDNA cloning, but also as diagnostic tools.

In a typical procedure for applying this technique of subtractive hybridization to investigate differences in the active genes of a certain sample of test or target cells, e.g. from tumour tissues, as compared with the active genes of a sample of reference cells, e.g. cells from corresponding normal tissue, total cell mRNA is extracted (using conventional methods) from both samples of cells. The mRNA in the extract from the test or target cells is then used in a conventional manner to synthesise corresponding single stranded cDNA using an appropriate primer and a reverse transcriptase in the presence of the necessary deoxynucleoside triphosphates, the template mRNA finally being degraded by alkaline hydrolysis to leave only the single stranded cDNA. In one particular version of the technique, important in the context of the present invention, care is taken to avoid unwanted synthesis of any second strand cDNA in this initial stage. The single stranded cDNA thus derived from the mRNA expressed by the test or target cells is then mixed under hybridizing conditions with an excess quantity of the mRNA extract from the reference (normal) cells. The latter is herein generally termed the subtractive hybridization "driver" since it is this mRNA or other single stranded nucleic acid present in excess which "drives" the subtraction process. As a result, cDNA strands having common complementary sequences anneal with the mRNA strands to form mRNA/cDNA duplexes and are thus subtracted from the single stranded species present. The only single stranded DNA remaining is then the unique cDNA that is derived specifically from the mRNA produced by glenes which are expressed solely by the test or target cells.

To complete the subtraction process and to use the single stranded unique cDNA, e.g. for producing labelled probes that may perhaps be used for detecting or identifying corresponding cloned copies in a cDNA clone colony (labelling of such probes is frequently introduced by using labelled deoxynucleoside triphosphates in synthesis of the cDNA), in the basic subtractive hybridization technique the common mRNA/cDNA duplexes are then physically separated out using, for example, hydroxyapatite (HAP) or, more preferably, (strept)avidin-biotin in a chromatographic separation method. After this operation, one or more repeat rounds of the subtractive hybridization may be carried out to improve the extent of recovery of the desired product.

From time to time various improvements in the basic technique outlined above have been introduced, including a method of chemical cross-linking subtractive hybridization (see Hampson et al (1992) *Nucleic Acids Res.* 20, 2899) which can enable the need for physical separation of the common mRNA/cDNA duplexes from single stranded unique cDNA to be avoided, but the process of producing labelled probes and/or cDNA subtraction libraries has still required a relatively large number of cells, especially since neither the target cDNA nor the driver RNA have been renewable. Although the introduction of PCR technology provided a new tool with a potential for enabling subtractive cloning to be applied to smaller numbers of cells and many strategies based on the hybridization of original target cDNA to so-called driver RNA or antisense cDNA have been developed to overcome the problem of limited starting cell number, problems have still remained. In particular, the methods developed have still been complex and have usually required multiple rounds of PCR and of subtractive hybridization which are liable to produce artifactual results by virtue of representational skewing during the amplification process.

One difficulty encountered in using PCR for amplifying cDNA is the fact that it cannot usually amplify efficiently full length cDNA strands corresponding to mRNA molecules from which they are derived, and when there is a mixture of cDNA strands or strand fragments covering a wide range of different lengths there is a tendency for preferential amplification to occur of the shorter length cDNA molecules. Ideally, for satisfactory PCR amplification of cDNA molecules, in order to reduce any non-uniformity and bias due to inefficient amplification of larger cDNA molecules the molecules in the reaction mixture upon which PCR amplification is performed should each have a size in the range of 100–500 base pairs, and within this range the sizes should be distributed randomly.

Obviously, it can also be important in using PCR amplification to provide amplified single stranded molecules that strand sense should be maintained.

SUMMARY OF THE INVENTION

It is accordingly one object of the present invention to provide an improved PCR-based process for achieving global amplification of nucleic acid nucleotide sequences especially suitable for providing material for carrying out subtractive hybridization, e.g. in connection with the study of differentially expressed mRNAs, and cDNAs derived therefrom.

It is also an object of the invention to provide a method by which a collection of single stranded nucleic acid molecules, such as for instance cDNA molecules derived from transcript cellular RNA, can be converted into a mixture of shorter DNA molecules having a random size or length distribution lying within a range, e.g. 100 to 500 base pairs, that is more suitable for achieving substantially uniform global PCR amplification representative of the original single stranded nucleic acid, while maintaining correct strand sense.

A further object of the present invention is to provide a method of processing samples of mRNA from a limited number of target and reference cells so as to provide amplified and renewable sources or single stranded target cDNA and driver nucleic acid for use in subtractive hybridization, especially in relation to the study of differential gene expression and the production of DNA hybridization probes of high specific activity.

These and other objects and features of the invention will become more clearly apparent from the description hereinafter contained.

In general, the invention involves a method of directional random oligonucleotide primed synthesis (herein abbreviated DROP) of cDNA to generate or produce a mixture of random Primed single-stranded nucleic acid fragments suitable for achieving substantially uniform global PCR amplification with maintenance of correct strand sense.

From one aspect, the invention provides a method of processing nucleic acid starting material composed of a collection of single stranded nucleic acid molecules so as to produce a mixture of shorter random length DNA fragments suitable for enabling substantially uniform global PCR amplification to be achieved yielding an amplified product representative of the total original single stranded nucleic acid, said method comprising the steps of:

(a) deriving from said nucleic acid starting material an immobilised set of first strand cDNA molecules each anchored at one end to a first solid phase support;

(b) carrying out a first random priming operation using said set of anchored first strand cDNA molecules as templates to synthesise a first set of random length single strand DNA fragments each incorporating at one end a first known nucleotide sequence and a terminal anchor group adapted to bind to complementary receptor material;

(c) separating said first set of random length single strand DNA fragments from the set of anchored first strand cDNA molecules;

(d) carrying out a second random priming operation using said first set of random length single strand DNA fragments as templates to synthesise a second set of single strand DNA fragments that each incorporate a second known nucleotide sequence at the opposite end to said first known nucleotide sequence;

(e) contacting the reaction mixture from (d) with a second solid phase support carrying receptor material complementary to said terminal anchor groups of said first set of random length single strand DNA fragments whereby said first set of random length single strand DNA fragments are anchored and immobilized on said second solid phase support;

(f) separating said newly synthesised second set of single strand DNA fragments from the immobilised first set of random length DNA fragments, said second set of single strand DNA fragments then providing a desired mixture of shorter random length single stranded DNA molecules suitable for subjecting to PCR amplification.

The nucleic acid starting material will generally comprise an extract of total mRNA obtained from a sample of cells so that the single-stranded nucleic acid molecules of which it is composed will be poly-A tailed mRNA strands, and in step (a) above the first strand cDNA molecules are synthesised therefrom using as primers deoxythymidine (dT) oligonucleotides anchored to solid support means such as magnetic beads or microspheres which facilitate separation of supernatant in subsequent operations.

In carrying out PCR amplification of the product from step (f) above, primers will generally be used which are matched to the known nucleotide sequences at opposite ends of the DNA fragments involved as hereinafter explained.

From another aspect the invention also provides a method for global PCR-based amplification of a collection of single stranded cDNA molecules synthesised as first strand cDNA from cellular transcript mRNA, said method including the steps of (a) providing an initial reaction mixture in which the strands of said cDNA molecules are immobilised by being anchored at one end to a first solid phase support via a polynucleotide sequence attached to the latter;

(b) carrying out a first random priming operation using said anchored first strand cDNA molecules as templates to synthesise a first set of random length single strand DNA fragments each incorporating at one end a first known nucleotide sequence and a terminal anchor group adapted to bind to complementary receptor material;

(c) separating said first set of random length single strand DNA fragments from the anchored first strand cDNA molecules;

(d) carrying out a second random priming operation using said first set of random length single strand DNA fragments as templates to synthesise a second set of single strand random length DNA fragments that each incorporate a second known nucleotide sequence at the opposite end to said first known nucleotide sequence;

(e) contacting the reaction mixture from (d) with a second solid phase , support carrying receptor material complementary to said terminal anchor groups of said first set of random length single strand DNA fragments whereby said first set of random length single strand DNA fragments are anchored and immobilized on said second solid phase support;

(f) separating said newly synthesised second set of random length single strand DNA fragments from the immobilised first set of random length DNA fragments; and (g) subjecting the said second set of random length single strand DNA fragments to at least one round of PCR amplification using primers matched to said known sequences at opposite ends.

In carrying out the first random priming operation a DNA polymerase such as that known under the Registered Trade Mark "Sequenase" which lacks exonuclease activity and does not cause strand displacement should be used so as to ensure that a collection of random size DNA fragments with terminal anchor groups will be generated. In contrast, however, in carrying out the second random priming operation it is desired to produce DNA fragments which are substantially full size copies of the fragments obtained from the first random priming operation, and a DNA polymerase which does produce strand displacement, such as Taq polymerase, should be used.

As already indicated, the DROP/PCR amplification process of the present invention can be particularly useful in conjunction with subtractive hybridization reactions, applied for example to the production of subtracted DNA hybridization probes for investigating and detecting differential gene expression between related tissue cells. In particular, the invention can enable small amounts of nucleic acid from limited cell numbers to be amplified in a reliable manner to provide sufficient material, both target cDNA and driver RNA, to carry out subtractive hybridization procedures. Moreover, the source of these materials can be renewable so that once the process of the invention has been carried out in relation to a particular sample of transcript RNA it should not be necessary subsequently to have to re-extract more of this RNA for subtraction operations.

For the purpose of providing amplified target cDNA for use in a subtractive hybridization procedure, at least the last round or rounds of PCR amplification will be carried out using at one end a primer which is labelled with an anchor group, such as biotin for instance, that can bind to a complementary receptor (avidin or streptavidin in the case of biotin) carried on solid support material, preferably magnetic beads or microspheres, whereby strand separation can readily be performed to produce the single stranded amplified cDNA required for subtractive hybridization. Before carrying out this last round or rounds of PCR amplifications with the biotinylated primer, in practice a portion of the reaction mixture can be retained and can be subsequently re-amplified thereby providing a renewable source of material for producing more of the target cDNA.

For providing amplified driver RNA it will generally be necessary to subject the PCR-amplified cDNA product to in vitro transcription using a suitable RNA polymerase, and the amplified cDNA must therefore include at least an appropriate promoter sequence for the chosen or selected RNA polymerase. This is conveniently introduced in carrying out the first random priming operation by using a so-called universal primer (degenerate oligonucleotide primer covering all possible combinations of the four DNA nucletide bases) that also incorporates the required promoter sequence, the latter additionally providing at least part of the aforesaid first known nucleatide sequence.

Again, before carrying out the in vitro transcription operation on the PCR-amplified cDNA product, a portion of the latter can be retained for subsequent re-amplification and use to provide a further supply of material for producing more of the "driver" RNA.

It will thus be appreciated that the invention also provides a method of processing samples of mRNA from a limited number of target and reference cells so as to provide amplified and renewable sources of single stranded target cDNA and driver nucleic acid for use in subtractive hybridization, especially in relation to the study of differential gene expression and the production of DNA hybridization probes of high specific activity, said method comprising treating the mRNA samples from the target cells and from the reference cells separately to produce an immobilised collection of first strand target cDNA molecules from the mRNA of the target cells and an immobilised collection of first strand "driver" cDNA from the mRNA of the reference cells, and then following the procedure outlined above for carrying out global PCR-based amplification for each separate cDNA collection.

The presently preferred above-mentioned first known nucleotide sequence is a T7 phage RNA polymerase initiator/promoter sequence which is incorporated in a universal primer employed in carrying out the first random priming operation of the DROP process, this sequence being placed in contiguous relationship with a biotin anchor group at the 5' terminal end of the primer. In practice, this primer is preferably a biotinylated T7 phage random hexamer primer.

Also, in preferred embodiments, the second known nucleotide sequence that is introduced in carrying out the second random priming operation is a restriction enzyme site sequence, e.g. an EcoR1 sequence, that is incorporated in a universal primer, preferably a random hexamer primer, used for said second random priming operation.

The presently preferred terminal anchor group which is introduced into the DNA fragments in at least the first random priming operation, and also in the PCR amplification of the target cell cDNA fragments, is biotin which is used in conjunction with complementary avidin or streptavidin receptor material carried by solid phase supports.

As mentioned, in carrying out the first random priming operation a DNA polymerase which lacks exonuclease activity and ability to cause strand displacement should be used, such as for example the T7 phage DNA polymerase sold under the "Sequenase II" (RTM). Also, since the concentration of the random hexamer or other universal primer affects the average size of the DNA fragments produced, this concentration should be adjusted so that the average size will be within the desired range 100 to 500 base pairs as far as possible. A further size selection will also usually be made in a later electrophoretic purification stage.

Also, in carrying out the second random priming operation a strand displacing DNA polymerase should be used, preferably a Taq polymerase which can strand displace and which has a polymerase dependent 5' to 3' exonuclease activity.

Strand separation of duplex molecules in the reaction mixtures will generally be carried out by heat denaturation followed by filtering or decanting off the supernatant, leaving the other one of the strands anchored to a said solid phase support.

It will also be appreciated that all the essential reagents for carrying out the method of processing nucleic acid starting material and/or global PCR-based amplification of cDNA in accordance with the invention, together with instructions for use, may be presented and marketed in the form of a kit, and such kits are also to be regarded as falling within the scope of the invention.

The invention, including a specific test example illustrating the manner in which it mavr be carried out in practice, will now be more fully described with reference to the accompanying drawings.

BRIEF DESCRIPTION OF THE DRAWINGS

In said drawings,

FIG. 3 is a diagram illustrating the composition and nucleotide sequences of the primers used in the example of FIGS. 1 and 2.

DETAILED DESCRIPTION OF SPECIFIC EMBODIMENT

The test example to be described relates to preparation of high specific activity radiolabelled DNA hybridization probes adapted for use in detecting and identifying differential expression in myeloid stem cells.

In this example, isolation of RNA from the myeloid stem cell line FDCP-Mix was performed by the method of Chomczynski et al (1987) *Anal Biochem*, 162 156–9, or was hybridised directly to oligo dT Dynabeads (Registered Trade Mark) as detailed by the manufacturer (Dynal Limited, UK). RNA from undifferentiated cells was regarded as being the target RNA and that from differentiated cells was regarded as being the reference or "driver" RNA for the purpose of subtractive hybridization.

Figure 1:
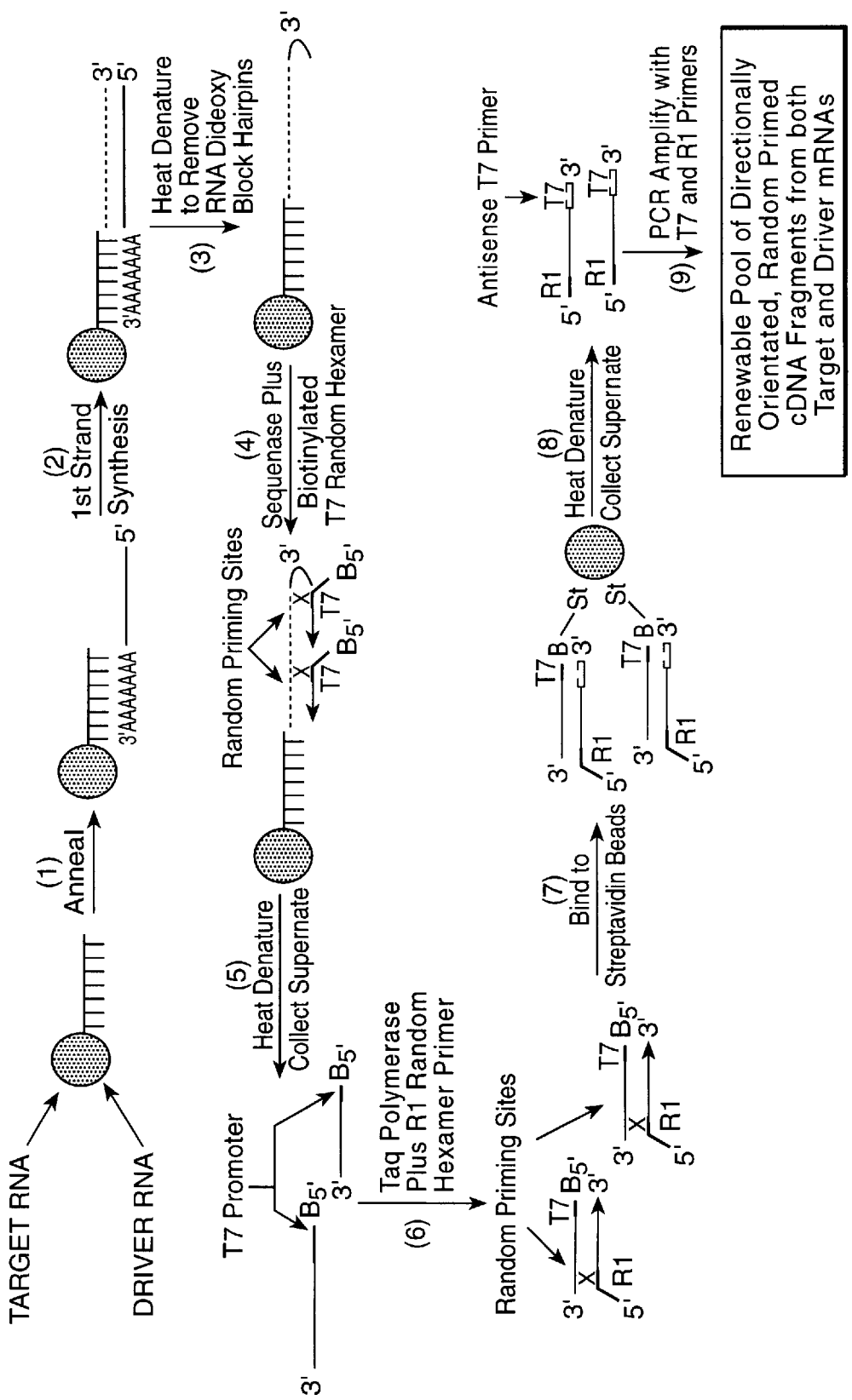
FIG. 1 is a diagrammatic summary of the different stages involved, labelled (1) to (9), in a specific example of the DROP process of the present invention in use for producing a mixture of random size DNA fragments suitable for subsequent efficient PCR amplification in order to provide material for subtraction hybridization in connection with a study of differential expression in myeloid stem cells.

The various reactions in the DROP process illustrated in FIG. 1 will first be briefly summarised below.

In Step 1, the target or the driver RNA was annealed to immobilised dT oligonucleotide molecules anchored at one end to magnetic beads (Dynabeads RTM). This was then followed by first strand cDNA synthesis in Step 2 to produce covalently immobilised cDNA. In Step 3 this material was heat denatured to remove the parental RNA template and the cDNA was dideoxv substituted in order to render any hairpin structure non-viable as polymerase primer sites. Unblocked hairpins would act as DNA polymerase priming sites with the effect that DNA synthesised from these would be covalently bound to the magnetic beads and thus lost from subsequent reactions. In Step 4 the first random primina operation was carried out using as the DNA polymerase a modified T7 DNA polymerase, Sequenase II (RTM) from Amersham International. This was chosen because of its inability to cause strand displacement and, more importantly at this stage, its lack of any exonuclease activity. A "universal" primer (see FIG. 3) was also used in this step having a nucleotide sequence

5' TGTAATACGA CTCACTATAG GGAGNNNNNN 3'—SEQ ID NO: 1 which includes the random hexamer primer sequence NNNNNN. A biotin anchor group was provided at the 5' end, and the nucleotide sequence also contained the T7 phage initiator/promoter sequence

5' TGTAATACGA CTCACTATAG GGAG 3'—SEQ ID NO: 2.

Thus, the products of step 4 were random primed fragments of cDNA (each having a 5' biotin terminal anchor group and T7 site) annealed along the immobilised parent cDNA strand. The size of these fragments was shown to be dependent on the concentration of primer used in the reaction and it was found that the optimal size range of 100 to 500 base pairs was produced using 0.1 μg/μl of reaction volume. This step 4 is a critical stage in the directional amplification strategy outlined, determining both the size and 5' position of the Biatin/T7 site.

In Step 5 the fragments from step 4 were released from the parent cDNA by heat denaturation and after filtering or decanting to remove the magnetic beads to which the parent cDNA molecules were anchored they were subjected in free solution to a second random priming operation (Step 6) using a universal random hexamer primer containing a random hexamer sequence and a restriction site sequence. In this example the primer had the nucleotide sequence

5' ATGAGAATTC GACGTCAGCC AGCNNNNNN 3'—SEQ ID NO: 3 which includes an EcoR1 (abbreviated R1) sequence (again see FIG. 3). This random prime reaction was catalysed by Taq polymerase which can strand displace and has a polymerase dependent 5' to 3' exonuclease activity. The products of this reaction should thus be complementary copies of the original T7 primed fragment which should increase in length with each successive priming event that occurs closer to the 3' end of the bictinylated strand until full length copies of the duplex strands of the original fragments formed in step 4 are eventually produced, i.e. there is in effect a single strand to duplex strand conversion. The Taq catalysed reaction, however, will initiate other secondary Ri hexamer priming events on any R1 primed strands displaced from the biotinylated T7 strand by the polymerase. This was a reason for incorporation of the biotin anchor group in step 4 as it enables selective binding to streptavidin (or avidin) coated beads to be carried out in Step 7 of all double stranded cDNAs which possess a 5' biotin/T7 site on one strand and a 5' R1 primer site on the other. Any other products of secondary priming events occurring in step 6 are removed at this stage.

In Step 8 denaturation released the non-biotinylated complementary strand which should have a 5' R1 primer at one end and a 3' antisense T7 orimer at the other. This product can thus then be PCR amplified using the T7 sequence primer SEQ ID NO: 2 and an R1 sequence primer 5' ATGAGAATTC GACGTCAGCC AGC 3'—SEQ ID NO: 4 (again see FIG. 3).

It has been reported previously that random primed PCR can be used to amplify target DNA non-specifically (see Degenerate Oligonucleotide-Primed (DOP) PCR Amplification Method described by H. Telenius et al (1992) Genomics 13, 718–725), and consequently the directional product herein described should be representative of all RNAs expressed by the target or driver cell type.

In more detail the individual reactions shown in FIG. 1 were performed as follows:

(1) Annealing

Between 10 and 50 μg of total RNAs isolated from both undifferentiated (target) and differentiated (driver) cells were annealed in separate reactions to oligo-dT Dynabeads (RTM) for 5 minutes at room temperature in 0.5M LiCl, 1% SDS, 10 mM EDTA.

(2) First strand synthesis

This was based on the method described by Raineri et al (1991) *Nucleic Acids Res*, 19, 4010. The Dynabeads (RTM) from step 1 were washed twice with 0.15M LiCl, 1% SDS, 5 mM EDTA and three times with 1×Superscript I (GIBCO BRL) buffer (50 mM Tris-HCl pH 8.3, 40 mM KCl, 6 mM $MgCl_2$, 0.1 mg/ml BSA), finally resuspending in 1×Superscript buffer with 0.25 mM of each dNTP (dATP, dGTP, dCTP, dTTP), 1 mM DTT plus 1 μg (200 units) Superscript I (TM) RNase H free reverse transcriptase (GIBCO ERL) and 5 units of placental ribonuclease inhibitor (Boehringer Mannheim) per 25 μl of reaction volume. This mixture was incubated at 37° C. with gentle agitation for 1 hour followed by extensive washing with 1×SSC, 0.1% SDS.

(3) Heat denaturation and dideoxy substitution

This was performed at 95° C. for four minutes in 1×SSC, 0.1% SDS and the beads were washed several times with PBS, 0.1% ultrapure BSA (GIBCO BRL). These were then resuspended in 1×Sequenase II buffer (40 mM Tris HCL pH 7.5, 20 mM $MgCl_2$, 50 mM NaCl, Amersham UK) plus 50 μM dideoxy NTPs and incubated at 37° C. for 10 minutes with 2 units of Sequenase II (RTM—Amersham UK). The beads were again washed extensively with PBS, 0.1% BSA.

(4) Biotinylated T7 random hexamer priming

The dideoxy hairpin blocked single stranded cDNA bound to the beads was then random primed with the biotinylated T7 random hexamer oligonucleotide having the nucleotide sequence SEQ ID NO: 1 (FIG. 3) using 0.1 g of primer/μl of reaction mix, 50 μM of each dNTP in 1×Sequenase buffer. This was heated to 68° C. for 2 minutes, cooled to 37° C., 3 units of Sequenase (RTM) were added and this mixture was maintained at 37° C. for 15 minutes with gentle agitation. The beads were washed with 5×100 μl of 1×SSC, 0.1% SDS at room temperature, 1×100 μl at 68° C. for 2 minutes and 2×100 μl of TE (50 mM Tris-HCl pH 7.5, 5 mM EDTA) at room temperature.

(5) Head Denaturation

The beads from step 4 were resuspended in 85 μl of 1×Tag polymerase buffer (10 mM Tris HCl pH 8.3, 1.5 mM $MgCo_2$, 0.5 M KCl), heated to 94° C. for 3 minutes and the supernatant was collected.

(6) R1 random hexamer priming

10 μg of R1 random hexamer primer having the nucleotide sequence SEQ ID NO: 3 (FIG. 3) and 50 μM final concentration of each dNTP were added to the supernatant from step 5. This was heated to 93° C. for 1 minute, cooled to 37° C. for 5 minutes and 2.5 units of Taq polymerase (Boehringer Mannheim) added. The incubation was continued at 37° C. for a further 5 minutes, then slowly increased to 72° C. over a period of 10 minutes.

(7) Binding to strertavidin beads The reaction mix from step 7 was added directly to 50 μM of prewashed (PBS 0.1% BSA) M280 streptavidin beads and incubated at room temperature with gentle agitation for 1 hour. The beads were washed at room temperature with 5×100 μl of PBS, 0.1% BSA, 1×100 μl at 68° C. for 2 minutes and 2×100 μl of TE at room temperature.

(8) Heat denaturation

The beads from sten 7 were resuspended in 85 μl of 1×Taq polymerase buffer, heated to 92° C. for 3 minutes and the supernatant collected.

(9) PCR amplification

In carrying out the PCR amplification of step 9 0.5 μg each of both the T7 and R1 primers SEQ ID NO: 2 and SEQ ID NO: 4 (FIG. 3) was added to the supernatant from step 8 together with 250 μM final concentration of each dNLP. 2.5 units of Taq polymerase were then added and the reaction was put through 25 cycles of, 94° C.-1 minute, 62° C.-1 minute, and 72° C.-1 minute.

A satisfactory size distribution and quality of the PCR product from step 9 was verified by carrying out an electrophoretic test on a small test sample of the product. Preparative 1.5% agarose gel electrophoresis was then carried out and DNA migrating between 150 and 500 base pairs was excised and electroeluted. Twenty separate 100 μl PCR reactions were then set up, 10 containing a 1 μl aliquot of electroeluted driver DNA (i.e. that derived from the driver RNA) and 10 containing a 1 μl aliquot of electroeluted target DNA (that derived from the target RNA). These were re-amplified using the same primers and conditions as in step 9 except that 12–14 cycles were used. All the products of the target DNA PCR reactions were pooled as were all those from the driver DNA PCR reactions, and 300 μl from each pool was purified by the use of a JET Pure PCR Reaction Purification Kit (Genomed, Hybaid, UK), ready for final preparation of single stranded amplified target cDNA and driver RNA as described below.

Preparation of single stranded amplified target cDNA

Figure 2:
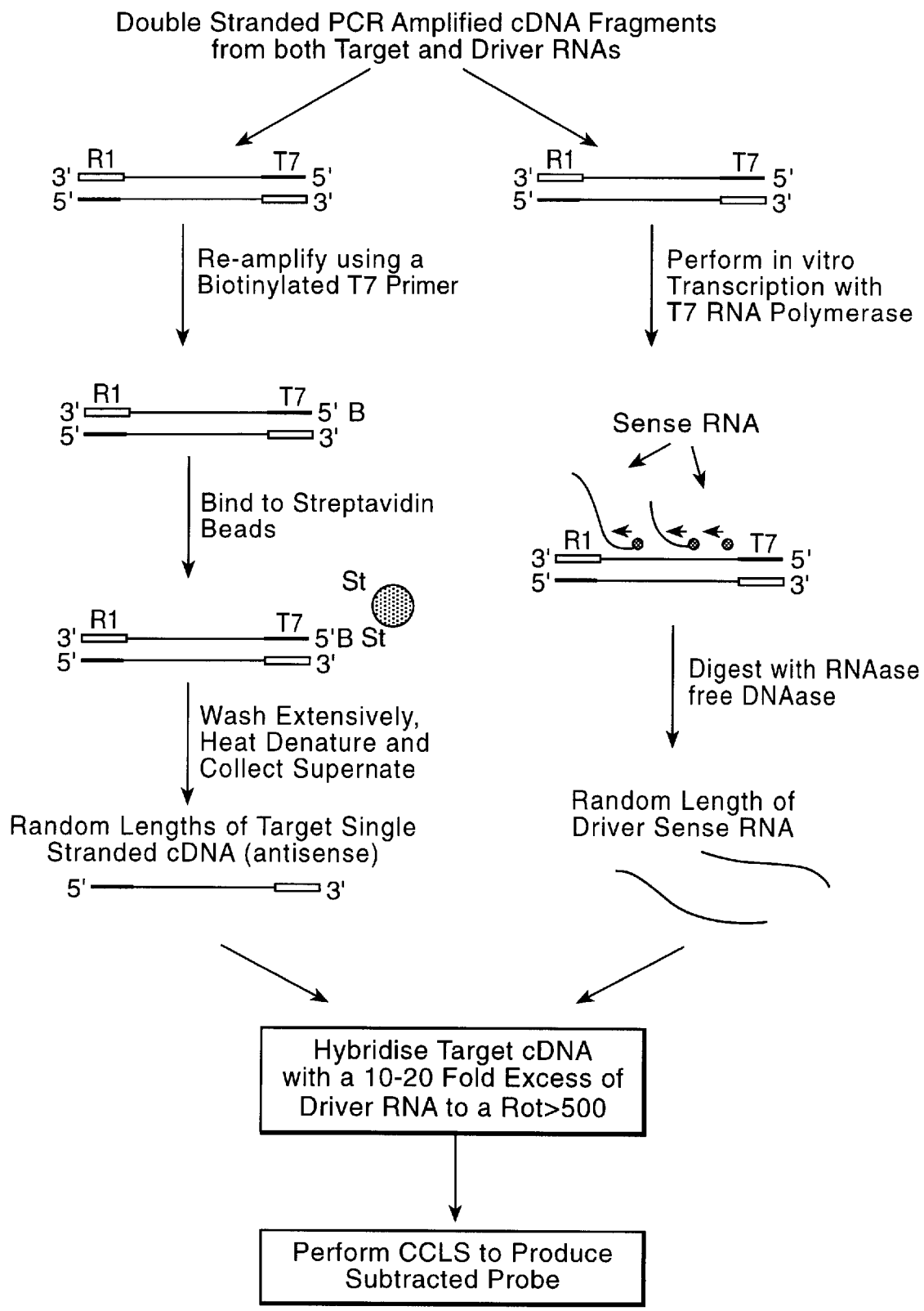
FIG. 2 is a diagrammatic summary or subsequent stages involved in producing PCR amplified single stranded target cDNA and driver RNA.

This is summarised in FIG. 2. Briefly, 3×100 μl separate PCR amplification reactions were set up with a 1 μl aliquot of the target (undifferentiated cell) JET purified PCR product using the same conditions described in step 9 except that a biotinylated T7 primer SEQ ID NO: 2 (see FIG. 3) was used for 12–14 cycles (if required, this reaction can be soiked with a small amount of α $^{32}$P dCTP to facilitate calculation of recovery yields) This PCR product was then bound to streptaviclin beads in the same way as in step 7 and these were washed with 5×100 μl PBS, 0.1% BSA at room temperature, followed by 2×100 μl at 68° C. for 2 minutes. Finally the beads were washed with 2×100 μl of TE, resuspended in 40 μl of TE and heated to 92° C. (no higher) for 3 minutes. The single stranded target cDNA was collected in the supernatant.

Preoaration of driver RNA

This is also summarised in FIG. 2 and made use of an in vit-o transcription kit (Boehringer Mannheim). Approximately 1 μg of driver (differentiated cells) JET purified PCR product was added to a reaction mix containing 1 mM of each NTP (ATP, CTP, GTP, UTP), 1×buffer (40 mM TrisHCL pH 8.0, 6 mM MgCl$_2$, 10 mM DTT, 2 mM spermidine), 40 units of T7 RNA polymerase, 20 units of placental ribonuclease inhibitor in a total volume of 40 μl, and this was incubated for 1 hour at 37° C. (Again the reaction can be spiked with a small amount of α $^{32}$P ATP to verify incorporation). 20 units of RNAase free DNAase (Promega, UK) were then added, the reaction mixture was incubated for a further 15 minutes at 37° C., extracted with an equal volume of 1:1 phenol/chloroform and RNA was precipitated using 3M ammonium acetate plus 2.5 volumes of 95% ethanol. The RNA was pelleted by centrifugation at 10,000×g for 15 minutes at 4° C., rinsed with 80% ethanol, redissolved in 30 μl of Milli Q (TM) sterile distilled water (Millipore) and reprecipitated from 0.3M sodium acetate polus 3 volumes of ethanol.

Subtractive hybridisation

The single stranded amplified target cDNA and driver RNA products could then be used in a subtractive hybridization process to produce a subtraction probe. In the present case, between 200 and 500 μg of target single stranded cDNA was co-pdrecipitated with 10 μg of in vitro transcribed driver RNA from 0.3M sodium acetate and three volumes of ethanol. This material was pelleted (10,000×g, 15 minutes), rinsed with 80% ethanol and dissolved in 2.5 μl of sterile Milli Q (TM) water to which was added 2.5 μl of 1M NaCl, 50 mM Hepes pH 7.5, 10 mM EDTA, 20% SDS. This mixture was heated to 95° C. for 1 minute, maintained at 68° C. for >24 hours (>R$_0$t 500 mol sec$^{-1}$) under a layer of liquid paraffin, diluted 5 fold with Ecterile water and precipitated from sodium acetate/ethanol.

In this particular examtle chemical cross-linking subtractive (CCLS) probe synthesis was then performed u sing 2,5-diaziridindl-1,4-benzdtauinone (DZQ) as previously described (see Hampson ed al (1992) *Nucleic Acids Res.* 20, 2899) except that the 68° C. treatment and addition of 5% DMSO immediately prior to cross linking were omitted.

As will be appreciated, the use of the biotinylated T7 amplification primer at the e sd of the PCR amplification process (FIG. 2) allows strand separation of the opposite strand to be carried out, thus providing an amplified source of single stranded target cDNA. it should be noted, however, that thorough washing of the streptavidin beads must be performed at this stage, prior to heat denaturation and elution of the target material, in order to prevent contamination with opposite strand sense DNA. This would have no counterpart in the driver RNA and hence would not be subtracted.

The directionality of the single stranded target cDNA product was confirmed by Southern blotting carried out in respect of both single and double stranded material which was then hybridised with equivalent amounts of α-actin antisense (A) and sense (B) riboporobes. It was found that an SP6 sense probe hybridised with both the single and double stranded material, whereas a T7 antisense probe hybridised with only the duplex product. It was also found that an α-actin antisense probe hybridised strongly with the in vitro transcription product whereas a corresponding sense probe showed a virtually undetectable signal, This indicated that the T7 RNA polymerase initiator/promoter secuence had been directionally incorporated such that sense RNA fragments were predominantly produced from the globally amplified cDNA. This was verified from both target and driver cDNAs.

Other hybridization tests in which random primed probes synthesised from total non-subtracted JET purified cDNA fragments produced from both target (undifferentiated) and driver (differentiated) RNAs were used against an undifferentiated cell cDNA library and also confirmed the global nature of the amplification process outlined.

In relation to the example described above it was also noted that the non-subtracted DROP, amplified target and driver cDNAs produced random primed probes that gave a whole range of signal intensities with a target undifferentiated cell cDNA library, indicating multiple sequence representation. Moreover, the undifferentiated minus differentiated subtracted probes produced a greater than 90% success rate in identifying sequences that were differentially expressed between the two cell types even though short exposure times (4 hours) and low wash stringency (0.8× SSC) were used.

Although most of the clones identified were in the moderate to high abundance class some of the remaining cDNAs were of considerably lower abuncance than this, indicating that the technique was quite sensitive. Also, it must be emphasised that the example herein described was carried out merely to demonstrate the application of the DROP process of this invention to subtractive hybridization cloning. Increasing the amount of single stranded target in the probe, higher wash stringency and longer exposure times should allow detection of lower abundance sequences.

The DROP procedure of this invention as herein described has several distinct advantages over existing methods. Some of these can be listed as follows:

(a) First, it is quick, requiring approximately two days.
(b) Second, it can be performed on limited cell numbers (the inventors have successfully produced DROP amplified cDNA from 10 µg of total cellular RNA).
(c) Third, the product can be used to synthesise both target single stranded cDNA and drinker RNA from the same amplified PCR product, thus readily allowing subtraction to be performed in both directions.
(d) Fourth, and most importantly, once the DROP product has been synthesised it is not necessary to re-extract more RNA for the purposes of subtraction.

Although there miaht be a possibility that some sequences may not amplify in a proportional manner which would artifactually skew their representation in the DROP product, the subtractive data obtained indicates a very high >95% success rate in identifying differentially expressed cDNAs. It is unlikely, therefore, that this represents a major problem.

Another possible source of error in relation to the particular example described could perhaps be the presence of an endogenous T7 RNA polymerase initiator/promoter sequence in the wrong orientation. This would produce antisense RNA as opposed to the sense product from the incorporated T7 site. However, since the DROP products are random primed fragments, it is likely that there will be many fragments represented that do not encompass the endogenous T7 site and will thus correctly produce sense RNA from the incorporated T7 primer. These would compete in the subtractive hybridization for anv complementary antisense RNA strands and thus lower the efficiency of hybridization to the target cDNA. However, in practice the results do not indicate that this possibility presents a problem.

The DROP technique as herein described can in fact rapidly produce a renewable source of both target and driver material from as little as $10^6$ cells, which material can be subsequently used for subtractive cloning.

Many modifications in respect of the specific details of the example herein described are of course possible within the scope of the invention, and the invention should be regarded as including all novel and inventive features and aspects herein disclosed, either explicitly or implicitly and either singly or in combination with one another. In particular, the invention is not to be construed as being limited by any illustrative example or by the terms and expressions used herein merely in a descriptive or explanatory sense. It is also to be pointed out that insofar as the terms "target cell source" and "reference or driver cell source" are used in the present specification in the context of denoting abnormal tissue cells and normal tissue cells respectively, on the assumption that the abnormal tissue cells are expressing genes not expressed in the normal tissue cells, in some cases abnormal tissue cells may be characterised by a failure to express genes that are expressed by the normal tissue cells. In that event, in carrying cut the invention the normal tissue cells should therefore be regarded as being the "target cell source" and the abnormal tissue cells would be regarded as being the "reference cell source" from which the subtractive hybridization driver nucleic acid would be derived.

We claim:

1. A method of processing nucleic acid starting material composed of a collection of single stranded nucleic acid molecules so as to produce a mixture of shorter directional random length DNA fragments suitable for enabling substantially uniform global PCR amplification to be achieved yielding an amplified product representative of the total original single stranded nucleic acid, said method comprising the steps of:

(a) deriving from said nucleic acid starting material an immobilised set of first strand cDNA molecules each anchored at one end to a first solid phase support;

(b) carrying out a first random priming operation using said set of anchored first strand cDNA molecules as templates to synthesise a first set of random length single strand DNA fragments each incorporating at one end a first known nucleotide sequence and a terminal anchor group adapted to bind to complementary receptor material;

(c) separating said first set of random length single strand DNA fragments from the set of anchored first strand cDNA molecules;

(d) carrying out a second random priming operation using said first set of random length single strand DNA fragments as templates to synthesise a second set of single strand DNA fragments that each incorporate a second known nucleotide sequence at the opposite end to said first known nucleotide sequence;

(e) contacting the reaction mixture from (d) with a second solid phase support carrying receptor material complementary to said terminal anchor groups of said first set of random length single strand DNA fragments whereby said first set of random length single strand DNA fragments are anchored and immobilized on said second solid phase support;

(f) separating said newly synthesized second set of single strand DNA fragments from the immobilised first set of random length DNA fragments, said second set of single strand DNA fragments then providing a desired mixture of shorter random length single stranded DNA molecules suitable for subjecting to PCR amplification.

2. A method as claimed in claim 1 of processing nucleic acid starting.material composed of a collection of single stranded nucleic acid molecules wherein said first random priming operation is carried out using a DNA polymerase which does not produce significant strand displacement and which is lacking in exonuclease activity.

3. A method as claimed in claim 2 of processing nucleic acid starting material composed of a collection of single stranded nucleic acid molecules wherein the DNA polymerase is a T7 phage DNA polymerase.

4. A method as claimed in claim 1 of processing nucleic acid starting material composed of a collection of single stranded nucleic acid molecules wherein said first random priming operation is carried out using a primer which is biotinylated to provide said terminal anchor group and which includes an RNA polymerase initiator/promoter sequence that provides said first known nucleotide sequence.

5. A method as claimed in claim 1 of processing nucleic acid starting material composed of a collection of single stranded nucleic acid molecules wherein the concentration of the primer used in said first random priming operation is adjusted such that the average size of at least the majority of the random length DNA fragments produced lies within the range of 100 to 500 base pairs.

6. A method as claimed in claim 1 of processing nucleic acid starting material composed of a collection of single stranded nucleic acid molecules wherein said second random priming operation is carried out using a DNA polymerase which is adapted to cause strand displacement.

7. A method as claimed in claim 6 of processing nucleic acid starting material composed of a collection of single stranded nucleic acid molecules in which said DNA polymerase used in the second random priming operation is Taq polyerase.

8. A method as claimed in claim 1 or processing nucleic acid starting material composed of a collection of single stranded nucleic acid molecules wherein said second random priming operation is carried out using a primer which includes a restriction enzyme site sequence to provide said second known nucleotide sequence.

9. A method as claimed in claim 1 of processing nucleic acid starting material composed of a collection of single stranded nucleic acid molecules wherein said second solid phase support is selected from avidin or streptavidin coated magnetic beads and avidin or streptavidin coated microspheres.

10. A method as claimed in claim 1 of processing nucleic acid starting material composed of a collection of single stranded nucleic acid molecules wherein the single-stranded nucleic acid molecules of the nucleic acid starting material are poly-A tailed mRNA strands from which said first strand cDNA molecules are synthesised in step (a) using complementay oligonucleotide primers anchored to said first solid phase support.

11. A mixture of random length single-stranded DNA molecules produced by a method as claimed in claim 1.

12. A method for global PCR-based amplification of nucleic acid starting material composed of a collection of single-stranded nucleic acid molecules, said method comprising processing said nucleic acid starting material in accordance with claim 1 to produce a mixture of shorter random length DNA molecules in the form of a said second set of random length single stranded DNA fragments, and then subjecting said mixture to at least one round of PCR amplification using primers matched to the known nucleotide sequences at opposite ends of the DNA fragments involved.

13. A method for global PCR-based amplification of a collection of single stranded cDNA molecules synthesised as first strand cDNA from cellular transcript mRNA, said method including the steps of
(a) providing an initial reaction mixture in which the strands of said cDNA molecules are immobilised by being anchored at one end to a first solid phase support via a polynucleotide sequence attached to the latter;
(b) carrying out a first random priming operation using said anchored first strand cDNA molecules as templates to synthesis a first set of random length single strand DNA fragments each incorporating at one end a first known nucleotide sequence and a terminal anchor group adapted to bind to complementary receptor material;
(c) separating said first set of random length single strand DNA fragments from the anchored first strand cDNA molecules;
(d) carrying out a second random priming operation using said first set of random length single strand DNA fragments as templates to synthesise a second set of single strand random length DNA fragments that each incorporate a second known nucleotide sequence at the opposite end to said first known nucleotide sequence;
(e) contacting the reaction mixture from (d) with a second solid phase support carrying receptor material complementary to said terminal anchor groups of said first set of random length single strand DNA fragments whereby said first set of random length single strand DNA fragments are anchored and immobilized on said second solid phase support;
(f) separating said newly synthesised second set of random length single strand DNA fragments from the immobilised first set of random length DNA fragments, and
(g) subjecting the said second set of random length single strand DNA fragments to at least one round of PCR amplification using primers matched to said known sequences at opposite ends.

14. A method as claimed in claim 13 for global PCR-based amplification of a collection of single stranded cDNA molecules synthesised as first strand cDNA from cellular transcript mRNA, wherein said first random priming operation is carried out using a DNA polymerase which does not produce significant strand displacement and which is lacking in exonuclease activity.

15. A method as claimed in claim 14 for global PCR-based amplification of a collection on single stranded cDNA molecules synthesised as first strand cDNA from cellular transcript mRNA, wherein the DNA polymerase is a T7 phage DNA polymerase.

16. A method as claimed in claim 13 for global PCR-based amplification of a collection of single stranded cDNA molecules synthesised as first strand cDNA from cellular transcript mRNA, wherein said first random priming operation is carried out using a primer which is biotinylated to provide said terminal anchor group and which includes an RNA polymerase initiator/promoter sequence that provides said first known nucleotide sequence.

17. A method as claimed in claim 13 for global PCR-based amplification of a collection of single stranded cDNA molecules synthesised as first strand cDNA from cellular transcript mRNA, wherein the concentration of the primer used in said first random priming operation is adjusted such that the average size of at least the majority of the random length DNA fragments produced lies within the range of 100 to 500 base pairs.

18. A method as claimed in claim 13 for global PCR-based amplification of a collection of single stranded cDNA molecules synthesised as first strand cDNA from cellular transcript mRNA, wherein said second random priming operation is carried out using a DNA polymerase which is adapted to cause strand displacement.

19. A method as claimed in claim 18 for global PCR-based amplification of a collection of single stranded cDNA molecules synthesised as first strand cDNA from cellular transcript mRNA, in which said DNA polymerase used in the second random priming operation is Taq polymerase.

20. A method as claimed in claim 13 for global PCR-based amplification of a collection of single stranded cDNA molecules synthesised as first strand cDNA from cellular transcript mRNA, wherein said second random priming operation is carried out using a primer which includes a restriction enzyme site sequence to provide said second known nucleotide sequence.

21. A method as claimed in claim 13 for global PCR-based amplification of a collection of single stranded cDNA molecules synthesised as first strand cDNA from cellular transcript mRNA, wherein said second solid phase support is selected from avidin or streptavidin coated magnetic beads and avidin or streptavidin coated microspheres.

22. A method as claimed in claim 13 for global PCR-based amplification of a collection of single stranded cDNA molecules synthesised as first strand cDNA from cellular transcript mRNA, wherein the average size of at least the majority of the random length DNA fragments produced which are subjected to PCR amplification lies within the range of 100 to 500 base pairs.

23. A method as claimed in claim 13 for global PCR-based amplification of a collection of single stranded cDNA molecules synthesised as first strand cDNA from cellular transcript mRNA, wherein said second set of random length single stranded DNA fragments is subjected to multiple rounds of PCR amplification, and at least the last round of said PCR amplification is carried out using at one end a primer which is labelled with an anchor group that can bind to a complementary receptor carried on solid support material, whereby strand separation can readily be performed to produce single stranded amplified cDNA as may be required for providing amplified target cDNA for use in a subtractive hydridization procedure.

24. A method as claimed in claim 13 for global PCR-based amplification of a collection of single stranded cDNA molecules synthesised as first strand cDNA from cellular transcript mRNA, wherein the PCR-amplified cDNA product is subjected to in vitro transcription using a selected RNA polymerase to produce single stranded RNA as may be required for providing amplified driver RNA for use in a subtractive hydridization procedure.

25. A method as claimed in claim 24 for global PCR-based amplification of a collection of single stranded cDNA molecules synthesised as first strand cDNA from cellular transcript mRNA, wherein said PCR-amplified cDNA product includes a promoter sequence matched to the selected RNA polymerase, said promoter sequence being incorporated by inclusion in primers used in carving out said first random priming operation and providing at least part of said first known nucleotide sequence.

26. A method of processing samples of mRNA from target cells and from reference cells so as to provide amplified and renewable sources of single stranded target cDNA and of driver nucleic acid for use in subtractive hybridization, said method comprising treating the mRNA samples from the target cells and from the reference cells separately to produce an immobilised collection of first strand target cDNA molecules from the mRNA of the target cells and an immobilized collection of first strand "driver" cDNA from the mRNA of the reference cells, and then carrying out global PCR-based amplification of the "target" cDNA collection to produce amplified target cDNA, and carrying out global PCR-based amplification of the "driver" cDNA collection in accordance with the method claimed in claim 24 to produce amplified driver RNA, wherein said global PCR-based amplification of the "target" cDNA collection is carried out using the method comprising the steps of:

(a) providing an initial reaction mixture in which strands of said cDNA molecules are immobilized by being anchored at one end to a first solid phase support via a polynucleotide sequence attached to the latter;

(b) carrying out a first random priming operation using said anchored first strand cDNA molecules as templates to synthesise a first set of random length single strand DNA fragments each incorporating at one end a first known nucleotide sequence and a terminal anchor group adapted to bind to complementary receptor material;

(c) separating said first set of random length single strand DNA fragments from the anchored first strand cDNA molecules;

(d) carrying out a second random priming operation using said first set of random length single strand DNA fragments as templates to synthesise a second set of single strand random length DNA fragments that each incorporate a second known nucleotide sequence at the opposite end to said first known nucleotide sequence;

(e) contacting the reaction mixture from (d) with a second solid phase support carrying receptor material complementary to said terminal anchor groups of said first set of random length single strand DNA fragments whereby said first set of random length single strand DNA fragments are anchored and immobilized on said second solid phase support;

(f) separating said newly synthesised second set of random length single strand DNA fragments from the immobilised first set of random length DNA fragments; and (g) subjecting said second set of random length single strand DNA fragments to at least one round PCR amplification using primers matched to said known sequences at opposite ends, wherein said second set of random length single stranded DNA fragments is subjected to multiple rounds of PCR amplification, and at least the last round of said PCR amplification is carried out using at one end a primer which is labeled with an anchor group that can bind to a complementary receptor carried on solid support material, whereby strand separation can readily be performed to produce single stranded amplified cDNA as may be required for providing amplified target cDNA for use in a subtractive hybridization procedure.

27. A subtractive hybridization process in which single stranded target cDNA derived from target cells is mixed under hybridizing conditions with an excess quantity of driver RNA derived from reference cells such that nucleic acid strands having common complementary sequences anneal to form duplex RNA/DNA molecules, characterised in that said single stranded cDNA and driver RNA are produced by processing respective samples of mRNA from target cells and from reference cells in accordance with the method claimed in claim 26.

28. A subtractive hybridization process as claimed in claim 27 wherein said duplex RNA/DNA molecules are subjected to chemical cross-linking using 2,5-diaziridinyl-1,4-benzoquinone (DZQ) or an analogous aziridinylbenzoquinone cross-linking agent.

* * * * *

UNITED STATES PATENT AND TRADEMARK OFFICE
CERTIFICATE OF CORRECTION

PATENT NO.   : 6,066,457
DATED        : May 23, 2000
INVENTOR(S)  : Hampson et al.

It is certified that error appears in the above-identified patent and that said Letters Patent is hereby corrected as shown below:

Please replace the current Abstract with the following new Abstract:

-- Nucleic acid starting material composed of a collection of single stranded nucleic acid molecules is anchored and processed by a directional random priming method to produce a mixture of shorter random size DNA molecules well-suited for achieving substantially uniform global PCR amplification. The processing and global amplification method disclosed is especially useful in conjunction with substractive hybridization procedures applied, for example, to the study of differential gene expression. --

Signed and Sealed this

Second Day of October, 2001

Attest:

*Nicholas P. Godici*

NICHOLAS P. GODICI
*Acting Director of the United States Patent and Trademark Office*

*Attesting Officer*

SEQUENCE LISTING

```
<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<221> NAME/KEY: primer_bind
<222> LOCATION: (1)..(30)
<223> OTHER INFORMATION: Nucleotide sequence is a T7 phage RNA
      polymerase initiator/promoter sequence which is incorporated
      in a universal primer where n can be at 25-30

<400> SEQUENCE: 1
tgtaatacga ctcactatag ggagnnnnnn                                      30

<210> SEQ ID NO 2
<211> LENGTH: 24
<212> TYPE: DNA
<213> ORGANISM: Artificial Sequence
```

```
<220> FEATURE:
<221> NAME/KEY: primer_bind
<222> LOCATION: (1)..(24)
<223> OTHER INFORMATION: Nucleotide sequence is a restriction enzyme
      site sequence which is incorporated in a universal primer

<400> SEQUENCE: 2
tgtaatacga ctcactatag ggag                                          24

<210> SEQ ID NO 3
<211> LENGTH: 29
<212> TYPE: DNA
<213> ORGANISM: Artificial Sequence
<220> FEATURE:
<221> NAME/KEY: primer_bind
<222> LOCATION: (1)..(29)
<223> OTHER INFORMATION: Nucleotide sequence includes an EcoR1 sequence
      incorporated in a universal primer where N at 24-29 can be any
      of a, t, g or c

<400> SEQUENCE: 3
atgagaattc gacgtcagcc agcnnnnnn                                     29

<210> SEQ ID NO 4
<211> LENGTH: 23
<212> TYPE: DNA
<213> ORGANISM: Artificial Sequence
<220> FEATURE:
<221> NAME/KEY: primer_bind
<222> LOCATION: (1)..(23)
<223> OTHER INFORMATION: T7 Phage Primer

<400> SEQUENCE: 4
atgagaattc gacgtcagcc agc                                           23
```